US00PP34764P2

(12) United States Plant Patent
Hartman

(10) Patent No.: US PP34,764 P2
(45) Date of Patent: Nov. 22, 2022

(54) ***CALADIUM* PLANT NAMED 'GPR OF16-241'**

(50) Latin Name: ***Caladium* X *hortulanum***
Varietal Denomination: 'GPR OF16-241'

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/741,088

(22) Filed: May 10, 2022

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — C. Anne Whealy

(57) ABSTRACT

A new and distinct cultivar of *Caladium* plant named 'GPR OF16-241', characterized by its compact and upright to mounding plant habit; dense, leafy and bushy appearance; vigorous growth habit and rapid growth rate; lance-type leaves that are greenish white in color, variably flushed with purplish pink and veins that are dark green in color and flushed with dark purple; leaves that occasionally have leafy appendages attached to the lower leaf surface and are similar in color to the leaves; and petioles that are close to black in color.

4 Drawing Sheets

Figure 1:
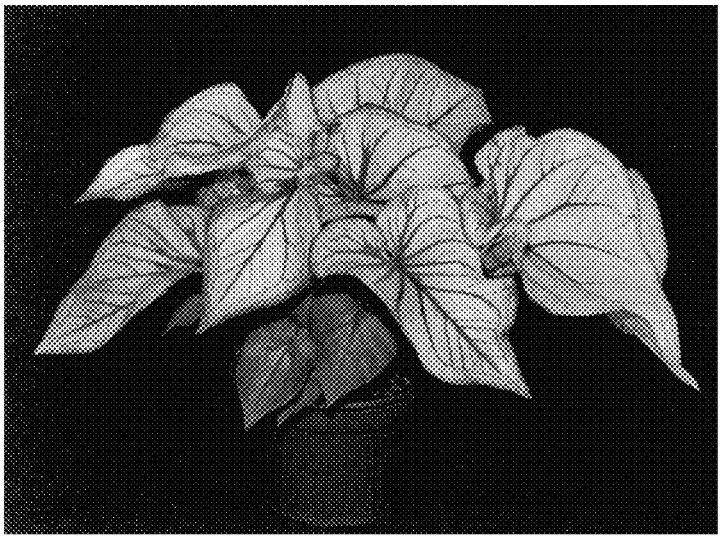

Botanical designation: *Caladium* X *hortulanum*.
Cultivar denomination: 'GPR OF16-241'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'GPR OF16-241'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2015 in Avon Park, Fla. of *Caladium* X *hortulanum* 'GPR SWT STR OF13-993', disclosed in U.S. Plant Pat. No. 33,470, as the female, or seed, parent with *Caladium* X *hortulanum* 'Florida Sweetheart', disclosed in U.S. Plant Pat. No. 8,526, as the male, or pollen, parent. The new *Caladium* plant was discovered and selected by the Inventor as a single plant within the progeny of the stated cross-pollination in a controlled outdoor nursery environment in Avon Park, Fla. in September, 2016.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2017 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'GPR OF16-241'. These characteristics in combination distinguish 'GPR OF16-241' as a new and distinct *Caladium* plant:

1. Compact and upright to mounding plant habit; dense, leafy and bushy appearance.
2. Vigorous growth habit and rapid growth rate.
3. Lance-type leaves that are greenish white in color, variably flushed with purplish pink and veins that are dark green in color and flushed with dark purple.
4. Leaves that occasionally have leafy appendages attached to the lower leaf surface and are similar in color to the leaves.
5. Petioles that are close to black in color.

Plants of the new *Caladium* differ primarily from plants of the female parent, 'GPR SWT STR OF13-993', in the following characteristics:

1. Plants of the new *Caladium* are shorter and more mounding than plants of 'GPR SWT STR OF13-993'.
2. Leaves of plants of the new *Caladium* are greenish white in color, variably flushed with purplish pink and veins that are dark green in color and flushed with dark purple whereas leaves of plants of 'GPR SWT STR OF13-993' are purplish red in color or white predominantly flushed with purplish red with dark purplish grey-colored venation and dark green-colored margins.
3. Leaf petioles of plants of the new *Caladium* are almost black in color whereas leaf petioles of plants of 'GPR SWT STR OF13-993' are black or brownish green in color with black-colored stippling, stripes and streaks.

Plants of the new *Caladium* differ primarily from plants of the male parent, 'Florida Sweetheart', in the following characteristics:

1. Leaves of plants of the new *Caladium* are greenish white in color, variably flushed with purplish pink and veins that are dark green in color and flushed with dark purple whereas leaves of plants of 'Florida Sweetheart' have dark pink-colored venation, rose pink-colored interveinal areas and greenish white-colored margins.
2. Leaf petioles of plants of the new *Caladium* are almost black in color whereas leaf petioles of plants of 'Florida Sweetheart' are tannish pink in color with brownish green-colored stripes and stippling.

Plants of the new *Caladium* can be compared to plants of *Caladium* X *hortulanum* 'Sangria', disclosed in U.S. Plant Pat. No. 26,263. In side-by-side comparisons, plants of the new *Caladium* differ primarily from plants of 'Sangria' in the following characteristics:

1. Plants of the new *Caladium* are shorter and more mounding than plants of 'Sangria'.
2. Leaves of plants of the new *Caladium* are greenish white in color, variably flushed with purplish pink and veins that are dark green in color and flushed with dark purple whereas leaves of plants of 'Sangria' have rose red-colored centers and contrasting dark green-colored margins.
3. Leaf petioles of plants of the new *Caladium* are almost black in color whereas leaf petioles of plants of 'Sangria' are tan to tannish pink in color occasionally with brown-colored stripes.

Plants of the new *Caladium* can also be compared to plants of *Caladium* X *hortulanum* 'Xplosion', disclosed in U.S. Plant Pat. No. 31,570. In side-by-side comparisons, plants of the new *Caladium* differ primarily from plants of 'Xplosion' in the following characteristics:

1. Leaves of plants of the new *Caladium* are greenish white in color, variably flushed with purplish pink and veins that are dark green in color and flushed with dark purple whereas leaves of plants of 'Xplosion' are dark green in color, tinged with greyed purple and with red purple to dark red-colored venation and interveinal areas that are white in color with light red-colored spots.
2. Leaf petioles of plants of the new *Caladium* are almost black in color whereas leaf petioles of plants of 'Xplosion' are greyed red, green and greyed green in color with dark brown-colored streaks and stipples.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'GPR OF16-241' grown in a container that has not had its tuber de-eyed prior to planting.

Figure 2:
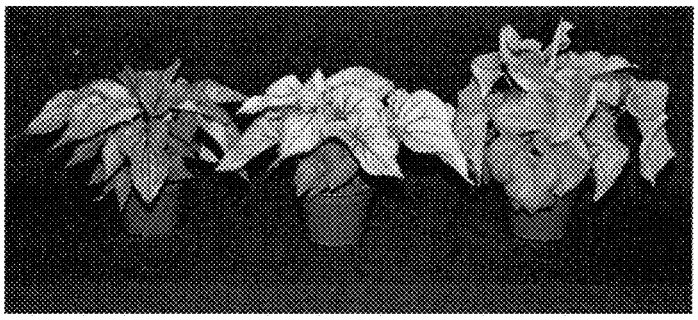

The photograph at the top of the second sheet (FIG. 2) is side perspective view of typical plants of the female parent, 'GPR SWT STR OF13-993' (left), 'GPR OF16-241' (center) and the male parent, 'Florida Sweetheart' (right).

Figure 3:
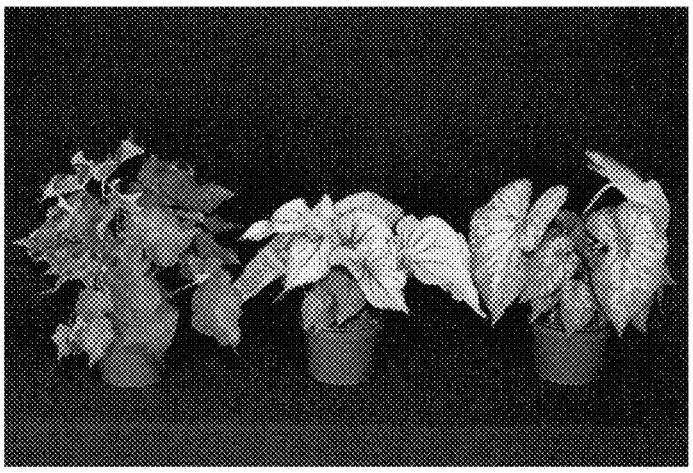

The photograph at the bottom of the second sheet (FIG. 3) is side perspective view of typical plants of 'Sangria' (left), 'GPR OF16-241' (center) and 'Xplosion' (right).

Figure 4:
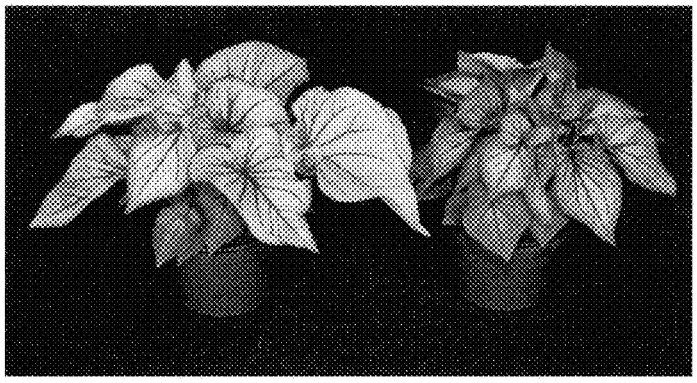

The photograph at the top of the third sheet (FIG. 4) is a comparison view of typical plants of 'GPR OF16-241' grown in containers, the plant on the left has not had its tuber de-eyed and the plant on the right has had its tuber de-eyed prior to planting.

Figure 5:
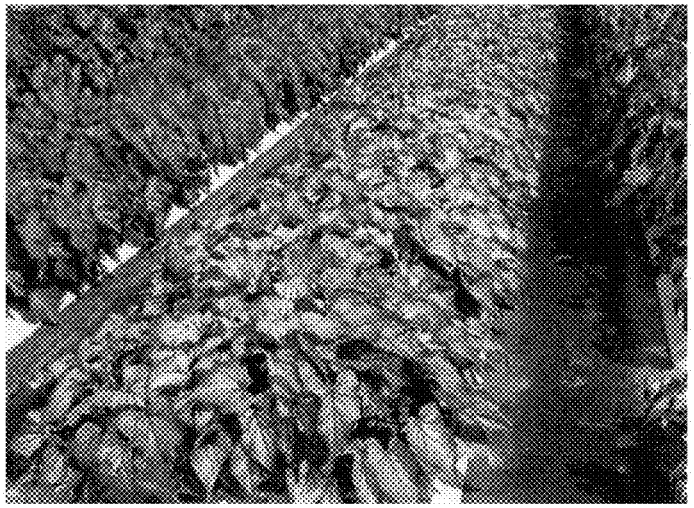

The photograph at the bottom of the third sheet (FIG. 5) is a side perspective view of typical plants of 'GPR OF16-241' grown in an open production field.

Figure 6:
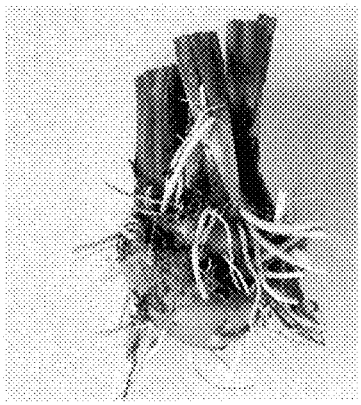

The photograph at the top of the fourth sheet (FIG. 6) is a close-up view of typical freshly-harvested tubers with roots and leaf petioles of 'GPR OF16-241'.

Figure 7:
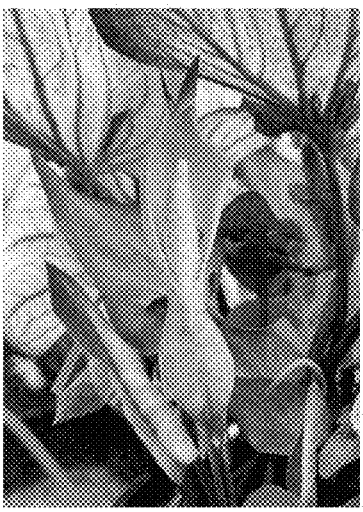

The photograph at the bottom of the fourth sheet (FIG. 7) is a close-up view of a typical inflorescence of 'GPR OF16-241'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were seven weeks old and plants grown in the outdoor nursery were six months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'GPR OF16-241'.

Parentage:

*Female, or seed, parent.*—*Caladium* X *hortulanum* 'GPR SWT STR OF13-993' disclosed in U.S. Plant Pat. No. 33,470.

*Male, or pollen, parent.*—*Caladium* X *hortulanum* 'Florida Sweetheart', disclosed in U.S. Plant Pat. No. 8,526.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented; individual segments are elliptic to irregular in shape. Height: About 2.5 cm to 3.1 cm. Diameter: About 4 cm to 6.2 cm. Segment height: About 2.1 cm to 2.5 cm. Segment diameter: About 2.3 cm to 3.2 cm. Axillary bud shape: Roughly triangular. Axillary bud height: About 3.5 mm. Axillary bud width: About 4 mm. Texture: Thick, starchy; somewhat brittle. Color: Periderm, freshly-harvested: Close to N199A. Periderm, dried: Close to 200A to 200B. Epidermis: Close to 159B; becoming closer to 159B to 159C with subsequent development. Cortical tissue: Close to 11C and 11D. Axillary buds: Close to 38B. Root description: Thick, fleshy contractile roots with few lateral branches; color, close to N155D, actual color of the roots is dependent on substrate composition, water quality, fertilizer type and formulation, substrate temperature and physiological age of roots. Rooting habit: Medium density.

Plant description:

*Plant type*.—Herbaceous perennial; suitable as a potted plant in containers 15-cm to 25-cm and suitable as a landscape plant in shaded areas.

*Plant and growth habit*.—Compact and upright to mounding plant habit; dense, leafy and bushy appearance; vigorous growth habit and rapid growth rate; potted plants finish in saleable form in about six weeks after planting tubers; leaf petioles and leaves arise from one or more growing points on tubers; leaf petioles initially upright and leaning outwardly with development.

*Plant height, from soil level to top of foliar plane, shade house-grown potted plants*.—About 20 cm to 24 cm.

*Plant height, from soil level to top of floral plane, shade house-grown potted plants*.—About 15 cm.

*Plant diameter, shade house-grown potted plants*.—About 38 cm to 43 cm.

*Number of shoots per plant, shade house-grown potted plants, tubers de-eyed*.—About nine to twelve develop per #1 tuber.

*Number of shoots per plant, shade house-grown potted plants, tubers not de-eyed*.—About three to four develop per #1 tuber.

*Cataphylls, shade house-grown potted plants*.—Length: About 5 cm. Width: About 9 mm. Shape: Lanceolate. Apex: Acute to emarginate. Base: Sheathing the stem. Texture and luster, outer and inner surfaces: Smooth, glabrous; semi-glossy. Color, outer surface: Close to 155C, streaked, stippled and flushed with close to 200A; distal end, close to 200A; color becoming closer to 200A stained with close to 187A with subsequent development. Color, inner surface: Close to 156D and 155C with colors and color patterns from outer surface visible.

Leaf description:

*Arrangement and type*.—Alternate; simple; lance-type; occasionally with leafy appendages attached to the lower leaf surface and similar in color to the leaves.

*Length, shade house-grown potted plants*.—About 12 cm to 15 cm.

*Width, shade house-grown potted plants*.—About 8.5 to 12 cm.

*Shape*.—Broadly ovate, cordate.

*Apex*.—Acute to acuminate.

*Base*.—Sagittate-peltate; cordate.

*Margin*.—Entire; mostly flat with broad undulations.

*Texture and luster, upper surface*.—Smooth, glabrous; thin; dull sheen.

*Texture and luster, lower surface*.—Smooth, glabrous; slightly glaucous; dull sheen.

*Venation pattern*.—Pinnate and palmate.

*Color, shade house-grown potted plants*.—When developing, upper surface: Background color: Close to NN155B or 155C variably tinged with close to 54C and/or 185D. Margins: Close to 187B. Basal notch: Close to 187C and 187D. Midvein: Close to NN137B, 177B and N186A. Lateral venation: Close to 137B, 177B and N186A; marginal venation, close to NN137B. Speckles: Close to NN137B and 155C. When developing, lower surface: Background color: Close to NN155A and NN155B tinged with close to 54D or close to N186A. Margins: Close to 187B. Basal notch: Close to 187A and 187C. Midvein: Close to 191B flushed with close to 177D variably mottled and streaked with close to 200A and 200B. Lateral venation: Close to 191C tinged with close to 177D and variably streaked with close to 200A and 200B; marginal venation, close to 191A tinged with close to 137D. Fully expanded leaves, upper surface: Background color: Close to 155C variably flushed with close to 65D and/or 185D. Margins: Close to 187B. Basal notch: Close to 187A and 187B. Midvein and lateral venation: Close to N186A and 187C tinged with close to 177B with occasional streaks, close to 147A; marginal venation, close to 147A and 147A flushed with close to 182C. Fully developed leaves, lower surface: Background color: Close to 62D. Margins: Close to 187B. Basal notch: Close to 187A and 187B. Midvein: Close to 191C flushed with close to 177D variably mottled and streaked with close to 200A and 200B. Lateral venation: Close to 191B and 191C tinged with close to 177D and variably streaked with close to 200B, 200C and 200D; marginal venation, close to 191A tinged with close to 189A.

*Petioles*.—Aspect: Initially upright and straight and leaning outwardly with development; flexible. Length, shade house-grown potted plants: About 11.5 cm to 21 cm. Diameter, distally, shade house-grown potted plants: About 3 mm to 3.5 mm. Diameter, proximally, shade house-grown potted plants: About 6 mm to 7 mm. Texture and luster: Smooth, glabrous; distally, glaucous. Color, shade house-grown potted plants: Close to 203A variably streaked with close to N170D or 199B and N199B stippled, streaked and tessellated with close to 200C; just below the leaf junction, close to 202A streaked with close to 181C or entirely, close to 203A. Wing length, shade house-grown potted plants: About 3 cm to 4 cm. Wing diameter, shade house-grown potted plants: About 5 mm. Texture and luster, inner and outer surfaces: Smooth, glabrous; dull sheen. Wing color, shade house-grown potted plants: Inner surface: Close to N155B, 156D and 155C; colors and patterns on the outer surface are visible on the inner surface. Outer surface: Close to 155C, densely streaked, stippled and flushed with close to 200A.

Inflorescence description:

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about eight weeks after growth commences; inflorescences last about three days before fading; inflorescences persistent.

*Spathe*.—Length, overall: About 8.5 cm. Length, distal open portion: About 5.7 cm. Length, proximal closed portion: About 2.8 cm. Width, distal open portion: About 2.4 cm. Depth, distal open portion: About 1.5 cm. Width, at constriction: About 8.5 mm. Width, proximal closed portion: About 1.7 cm. Shape, open portion: Elliptic to obovate. Apex: Acuminate. Base: Acute. Margin: Entire. Texture and luster, front surface: Smooth, glabrous; dull sheen. Texture and luster, rear surface: Smooth, glabrous; dull sheen; proximally, glaucous. Color, front surface: Distal open portion: Close to 155C and 145D; with subsequent development, distally becoming closer to N199A. Proximal closed portion: Close to 147D; color does not change with subsequent development. Color, rear surface: Distal open portion: Close to 146D and 145C; color does not change with subsequent development. Proximal closed portion: Close to 147C with areas and streaks, close to 147B; color does not change with subsequent development.

*Spadix*.—Length, overall: About 5.6 cm. Length, male flower zone: About 2.4 cm. Length, sterile zone: About 1.2 cm. Length, female flower zone: About 2 cm. Diameter, male flower zone: About 5 mm. Diameter, sterile flower zone: About 3 mm. Diameter, female flower zone: About 6 mm. Shape: Columnar, spindle-shaped. Apex: Acute. Base: Obtuse. Aspect: Upright. Color, mature, male zone: Close to 155D. Color, mature, sterile zone: Close to 155C to 155D. Color, mature, female zone: Close to 158D. Male flowers: Quantity per spadix: About 68. Shape: Obovate. Height: About 1.5 mm. Diameter: About 2 mm. Pollen amount: Sparse to moderate. Pollen color: Close to 4D. Female flowers: Quantity per spadix: About 80. Shape: Obovate. Height: About 2 mm. Diameter: About 1.2 mm. Stigma color: Close to 158D. Ovary color: Close to 11D.

*Scapes*.—Length: About 9.4 cm. Diameter: About 3.5 mm. Strength: Sturdy; somewhat flexible. Aspect: Mostly erect, straight. Texture and luster: Smooth, glabrous; slightly glossy to slightly glaucous. Color: Close to 199C and 199D streaked and striped with close to 200A; just below the spathe, close to 199C and 199D streaked and striped with close to 200A and flushed with close to 147C and 147D.

*Seeds and fruits*.—To date, seed and fruit development have not been observed on plants of the new *Caladium*.

Pathogen tolerance/resistance: Plants of the new *Caladium* have been observed to have average tolerance to *Pythium* Root Rot and average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'GPR OF16-241' as illustrated and described.

* * * * *